United States Patent [19]

Backes

[11] Patent Number: 5,024,080
[45] Date of Patent: Jun. 18, 1991

[54] PAINT VISCOSITY MONITORING SYSTEM AND METHOD

[75] Inventor: Peter G. Backes, Canoga Park, Calif.

[73] Assignee: Hughes Aircraft Company, Los Angeles, Calif.

[21] Appl. No.: 503,586

[22] Filed: Apr. 3, 1990

[51] Int. Cl.⁵ .............................................. G01N 11/00
[52] U.S. Cl. .......................................... 73/54; 73/64.4
[58] Field of Search ................................. 73/54, 64.4

[56] References Cited
FOREIGN PATENT DOCUMENTS

| | | | |
|---|---|---|---|
| 492787 | 2/1976 | U.S.S.R. | 73/54 |
| 1188588 | 10/1985 | U.S.S.R. | 73/54 |
| 1242764 | 7/1986 | U.S.S.R. | 73/54 |
| 1260747 | 9/1986 | U.S.S.R. | 73/54 |
| 1430828 | 10/1988 | U.S.S.R. | 73/56 |

Primary Examiner—Hezron E. Williams
Assistant Examiner—Joseph W. Roskos
Attorney, Agent, or Firm—M. E. Lachman; W. J. Streeter; W. K. Denson-Low

[57] ABSTRACT

A system and method for measuring viscosity of a layer of wet paint on a surface by deforming the layer of paint, measuring the response of the deformed layer of paint, and determining the viscosity based on the measured response.

17 Claims, 1 Drawing Sheet

PAINT VISCOSITY MONITORING SYSTEM AND METHOD

BACKGROUND OF THE INVENTION

1. Field of the Invention

The present invention relates generally to a method for measuring the viscosity of paint. More particularly, the present invention relates to a system and method for measuring the viscosity of a layer of wet paint after it has been applied to a surface.

2. Description of Related Art

The measurement and control of paint viscosity is an important part of any paint application process. Viscosity measurements are especially important in spray painting systems where small variations in paint viscosity can drastically affect the quality, durability and appearance of the paint coating.

Typically, the viscosity of paint is monitored while the paint is still in a spray tank and prior to applying the paint to a surface. A standard liquid viscometer is utilized for this type of paint viscosity monitoring. The results of the paint viscosity monitoring are used to determine the propensity of the paint to run, sag, or peel.

The problem with measuring paint viscosity prior to application is that the actual viscosity of the paint layer on the painted surface is usually different from the viscosity measured in the spray tank. Accordingly, measurement of paint viscosity in the spray tank only provides an indirect indication of the actual viscosity of the paint at the application site. Changes in parameters which may occur during the operation of the painting system can result in the surface viscosity of the applied paint changing while the viscosity of the paint in the spray tank remains the same. Unfortunately, such variations are only noticed when the applied paint layer runs, sags or otherwise becomes unacceptable.

The most desirable method for measuring and monitoring paint viscosity would be to measure the viscosity of the paint after it has been applied to a surface. Direct viscosity measurement of the layer of paint after application is more meaningful because it provides a direct indication of the likelihood of the paint to run, sag or peel. Further, direct measurements of the viscosity of the applied layer of paint can be made at selected times after application to provide direct information on paint curing behavior. There are also numerous other advantages which are inherent in being able to directly measure the viscosity of paint once it is applied to a surface. As in any measurement or monitoring system, direct measurement of a parameter, such as viscosity, is preferable to indirect measurement.

Although there are numerous advantages inherent in measuring the viscosity of paint at the application site, a major problem involves being able to make such direct measurements without destroying or otherwise permanently disturbing the paint layer. Destruction or disturbance of the paint layer is especially undesirable for automobiles, airplanes, appliances, and the like, where a flawless finish is important.

As is apparent from the above, it would be desirable to provide a system and method for directly monitoring the viscosity of a layer of wet paint on a surface during the painting process. Further, the process must be non-destructive in that the disturbance or destruction of the paint is minimized. Such a non-destructive and direct testing method would enable one to more accurately control paint viscosity to avoid the running, sagging, and peeling of paint which may result when viscosity is measured only in the spray tank.

SUMMARY OF THE INVENTION

In accordance with the present invention, an apparatus and method are provided for directly measuring the viscosity of a layer of wet paint on a substrate. This direct measurement is made without destroying or otherwise permanently disturbing the painted surface.

The present invention is based on the discovery that the response of a liquid layer of paint to minor deformations in the paint layer can be used to provide a measure of the paint viscosity. The invention involves applying a deforming force to a predetermined area of the exposed layer of paint and then measuring the response of the exposed outer surface to the deforming force. The measured response is then used to determine the viscosity of the paint. This procedure enables one to directly determine and control paint viscosity at the application site without permanently altering the surface coating.

As a feature of the present invention, the deformation force may be provided by pulses of compressed gas which form a small dimple in the paint layer. The responses of the paint layer during formation of the dimple and/or during return to the non-disturbed state are measured to provide a direct indication of paint viscosity.

As another feature of the present invention, the response of the paint layer to the deforming force is measured optically. This is accomplished by reflecting a collimated light beam off of the deformed area before, during and after deformation. The changes in light reflection are used to directly measure the response of the paint layer from which viscosity can be determined.

As an additional feature of the present invention, viscosity information may be obtained by measuring the response of the paint layer during either deformation or restoration or during both deformation and restoration.

The above-discussed and many other features and attendant advantages of the present invention will become apparent as the invention becomes better understood by reference to the following detailed description when considered in conjunction with the accompanying drawings.

DESCRIPTION OF PREFERRED EMBODIMENTS

The system and method of the present invention may be used to monitor the viscosity of a layer of wet paint on a substrate in a wide variety of circumstances. However, the system and method are especially well-suited for monitoring the viscosity of a layer of wet paint which has been applied to a surface of an automobile, airplane, appliance or any item where it is desirable to not disturb or destroy the painted finish of the article. The system and method of the present invention are also well-suited for use during an automated painting process.

The following description will describe the monitoring of paint viscosity on a substantially flat substrate with it being understood that the invention may be used to monitor paint viscosity in other situations. In addition, the following description will be limited to a preferred embodiment wherein the paint layer is deformed with a pulse of gas and the response is optically measured. It will be understood that other deforming forces, such as the application of a directed vacuum or utilization of liquid deforming forces may also be used provided that the paint layer is not permanently damaged. Further, other measurement systems based on mechanical or acoustic monitoring are possible provided that they do not interfere with the response of the paint to the deforming force.

In accordance with the present invention, the layer of paint applied to the substrate is deformed by a pulse of gas emitted from a compressed gas nozzle to form a dimple or depression in the paint layer. Gases which may be used include air, nitrogen or any other gas which does not react with or otherwise adversely affect the paint. Air is the preferred gas and it should be relatively moisture free.

The size and shape of the depression or dimple is a function of the gas pressure at the gas nozzle, the dimensions of the nozzle, distance of the nozzle to the substrate, thickness of the paint layer and viscosity of the paint layer. The size of the dimple formed by a given gas pulse is not important in providing a useful measure of viscosity. It is preferred, however, that the size of the dimple be kept as small as possible in order to minimize any residual disturbance of the paint layer. Depressions having diameters of less than 0.5 inch (1.27 cm) are preferred.

In accordance with the present invention, by measuring the time required to deform the smooth surface of the paint and/or the time required for the smooth surface to be restored after deformation, the above-mentioned variables other than viscosity are eliminated. The viscosity of the paint can therefore be determined by measuring the time required to deform the layer of paint and/or the time required for the paint layer to return to its original shape.

Figure 1:
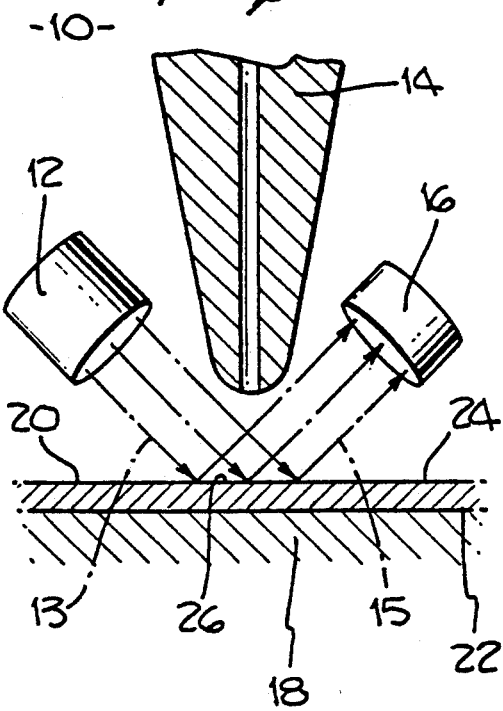
FIG. 1 is a representation of a preferred system in accordance with the present invention for monitoring the viscosity of a layer of wet paint on a surface showing the layer of paint in a non-deformed condition.
Figure 2:
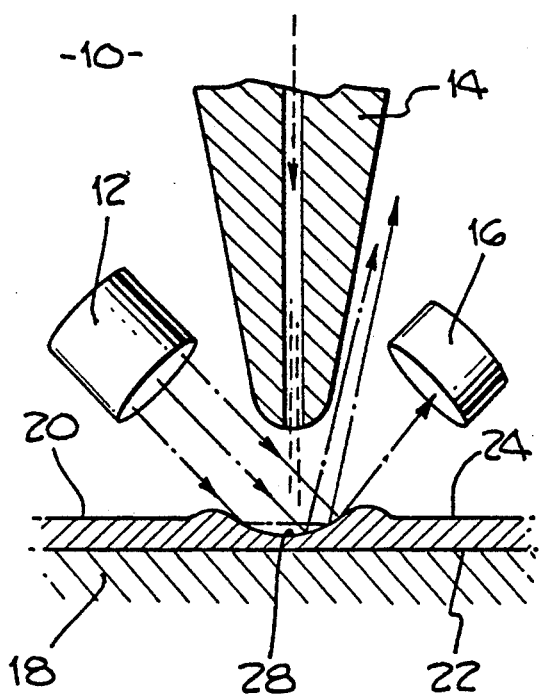
FIG. 2 is a representation of a preferred system in accordance with the present invention showing the layer of paint in a deformed condition.

A preferred exemplary system in accordance with the present invention is shown generally at 10 in FIGS. 1 and 2. FIGS. 1 and 2 show the system 10 as used on a layer of wet paint 20 applied to a substantially flat substrate 18. The layer of wet paint 20 may be further defined as having an inner surface 22 adjacent to the substrate 18 and an exposed outer surface 24.

As shown in FIG. 1, a collimated light source 12 emits a collimated light beam as indicated by arrows 13. The collimated light beam reflects off of a predetermined area 26 of the exposed outer surface 24 of the layer of paint 20. The intensity of the reflected light is measured by a directional spot light meter 16. When the predetermined area 26 of the exposed outer surface 24 is in a non-deformed condition, as in FIG. 1, the light reflects off of the pre-determined area 26 in a substantially collimated form as indicated by arrows 15. Therefore, the light intensity reflected off of the non-deformed predetermined area 26 is at a maximum value. Also shown in FIG. 1 is air nozzle 14 which is connected to the necessary equipment (not shown) to provide a pulsed jet of air against the paint layer 20.

FIG. 2 shows the system 10 with the compressed air nozzle 14 turned on. The compressed air nozzle 14 emits a brief pulse of compressed air onto the predetermined area 26 of the exposed outer surface 24 of the layer of paint 20. The brief pulse of compressed air deforms the exposed outer surface 24 of the layer of paint 20, forming a dimple 28 on the exposed outer surface 24 of the layer of paint 20. The duration of the pulse is preferably on the order of a second or less. However, longer pulse times are possible, especially where the paint has a high viscosity or where response of the paint is to be measured only after the depression has been formed.

The collimated light source 12 continues to reflect a collimated light beam off of the predetermined area 26 during the deformation of the predetermined area 26. The directional spot light meter 16 also continues to measure the intensity of the reflected light during the deformation of the predetermined area 26. However, as shown in FIG. 2, when the predetermined area 26 is deformed, the light reflected off of the predetermined area 26 is diffused. Thus, the measured light intensity reflected off of the dimple 28 in the predetermined area 26 is lower than the light intensity reflected off of the non-deformed predetermined area 26.

Figure 3:
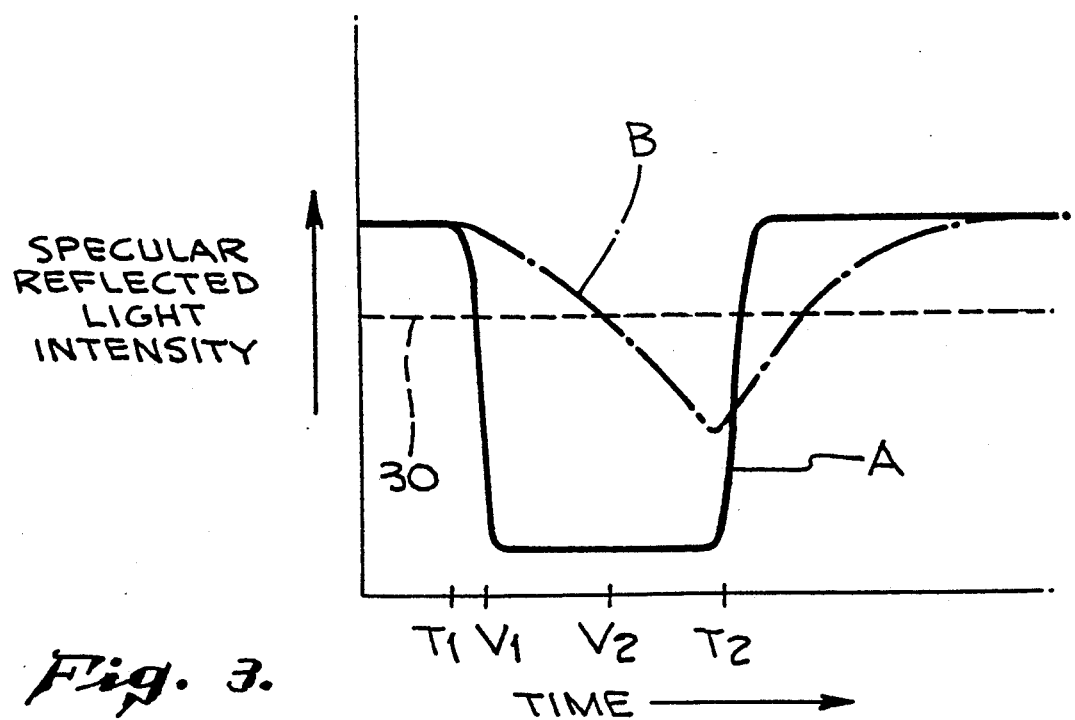
FIG. 3 is a graph of the reflected light intensity versus time showing the measured response produced by the present invention of a high viscosity paint and a low viscosity paint.

Referring now to FIG. 3, a graph of reflected light intensity versus time is shown. A threshold level 30 of reflected light intensity is shown on the graph. The threshold level 30 corresponds to the amount of reflected light intensity measured at the point in time when the outer surface 24 of the layer of paint 20 initially deforms due to the brief pulse of compressed air. Different threshold levels may be used, provided that the threshold level remains constant during operation of the system.

The selected reflectance threshold level should be sufficiently below the undisturbed reflectance level so that it provides an adequate measure of surface deformation. As shown in FIG. 3, the threshold level is preferably reached prior to final or fully developed distortion of the surface, i.e., the threshold reflectance is preferably not chosen at the minimum reflectance measured during the deformation. When only measuring the restoration of the layer to its original shape after the pulse of gas is released, the threshold reflectance level may be selected as being nearer to the reflectance of the undisturbed surface. (The time becomes very extended if the threshold is set to the full reflectance for surface restoration.) However, when the deformation or response to the initial application of the gas pulse is being measured, the threshold reflectance level must be at least slightly below the undisturbed reflectance level in order to provide a measurement of the initial surface deformation (See FIG. 3).

As previously described, the intensity of the light reflected off of the predetermined area 26 is measured by the spot light meter 16. This intensity is represented on the vertical axis of the graph in FIG. 3. The intensity is measured over time, with time being represented on the horizontal axis of the graph. Referring to the horizontal axis of the graph, $T_1$ and $T_2$ are shown. $T_1$ marks the point at which the air nozzle 14 is turned on and the brief pulse of air is first emitted from the compressed air nozzle 14. $T_2$ marks the point at which the air nozzle 14 is turned off and the brief pulse of air is no longer emitted from the air nozzle 14.

In order to determine the paint viscosity of the layer of paint 20, the amount of time required for the outer surface 24 of the predetermined area 26 to deform (deformation time) after the compressed air nozzle 14 is turned on must be measured. Optionally, the time required for the deformed surface to restore itself to its original condition (restoration time) after the compressed air nozzle 14 is turned off can also be measured. As another option, just the restoration time may be measured. The deformation time and/or restoration time are measured by determining the amount of time required for the reflected light intensity to drop below the threshold level 30 after the air nozzle 14 is turned on ($T_1$), and/or the amount of time required for the reflected light intensity to reach the threshold level 30 after the air nozzle 14 is turned off ($T_2$). It should be noted that different threshold levels may be used for the measurement of the deformation time and for the measurement of restoration time.

Referring again to the horizontal axis of the graph shown in FIG. 3, $V_1$ marks the point on curve A at which the reflected light intensity drops below the threshold level 30 for a low viscosity paint. $V_2$ marks the point on curve B at which the reflected light intensity drops below the threshold level 30 for a high viscosity paint. As can be seen by the graph, the reflected light intensity of a high viscosity paint (curve B) requires more time to drop below the threshold level 30 than does a low viscosity paint (curve A). Therefore, by analyzing the time necessary to deform the predetermined area 26 and the time for a smooth surface to be restored, the viscosity of the layer of paint 20 on the substrate 18 may be determined.

The system and method disclosed is well suited for use during an assembly line painting process. The system provides non-destructive monitoring of the viscosity of the layer of wet paint 20. Therefore, the system may be used during the painting process without requiring repair of the monitored surfaces. If the system is used with a robotic painting process, the system may be mounted on a separate robot, or on the spray painting robot. Furthermore, the reflected light intensity data and the measured deformation and restoration time may be collected and analyzed under conventional computer control procedures.

Once an acceptable paint viscosity is established for a given surface, then the deformation response in accordance with the present invention can be measured. Subsequent tests of deformation responses for surfaces painted later can then be measured and compared to the initial response to monitor any changes in viscosity. If desired, paint layers with known viscosities may be measured in accordance with the present invention and a standard set of curves developed to provide an accurate quantitative determination of actual viscosity. The generation of such standard curves and continual monitoring of mass produced painted articles is preferably conducted under computer control.

Having thus described exemplary embodiments of the present invention, it should be noted by those skilled in the art that the within disclosures are exemplary only and that various other alternatives, adaptations and modifications, may be made within the scope of the present invention. Accordingly, the present invention is not limited to the specific embodiments as illustrated herein, but is only limited by the following claims.

What is claimed is:

1. A method for measuring the viscosity of a layer of wet paint comprising the steps of:
   providing a substrate having a layer of wet paint thereon, said layer of wet paint having an inner surface adjacent to said substrate and an exposed outer surface having an original shape;
   applying a deforming force to a predetermined area of the exposed outer surface of said layer of wet paint to depress said outer surface toward said inner surface to form a dimple in said layer of wet paint;
   measuring the time required to deform said outer surface to form said dimple; and
   determining the viscosity of the layer of wet paint based on said time measured.

2. A method according to claim 1 further comprising after measuring said time required to deform said outer surface, releasing said deforming force and measuring the time required for said outer surface to return to said original shape.

3. A method according to claim 2 wherein the step of measuring said time required for said outer surface to return to said original shape further comprises the steps of:
   reflecting a collimated light beam off of said dimple;
   measuring the intensity of the light reflected off of said dimple;
   determining a threshold level of reflected light intensity, said threshold level being the level of light intensity reflected from said outer surface without said dimple being present; and
   measuring the time required for the reflected light intensity to reach the threshold intensity.

4. A method according to claim 3 wherein the intensity of the reflected light is measured by a directional spot light meter.

5. A method according to claim 2 wherein the step of measuring said time required for said outer surface to return to said original shape is accomplished through automated computer control.

6. A method according to claim 1 wherein the step of measuring said time required to deform said outer surface comprises the steps of:
   reflecting a collimated light beam off of said predetermined area;
   measuring the intensity of the light reflected off of said predetermined area;
   determining a threshold level of reflected light intensity, said threshold level being less than the reflected light intensity from the exposed outer surface prior to said deforming force being applied; and
   measuring the time required for the reflected light intensity to drop below the threshold level.

7. A method according to claim 6 wherein the intensity of the reflected light is measured by a directional spot light meter.

8. A method according to claim 1 wherein said deforming force is a pulse of compressed gas emitted onto said predetermined area.

9. A method according to claim 1 wherein the step of measuring the time required to deform said outer surface is accomplished through automated computer control.

10. A method according to claim 1 wherein the step of determining the viscosity of the wet paint is accomplished through computer control.

11. An apparatus for measuring the viscosity of a layer of wet paint on a substrate, said layer of paint having an inner surface adjacent to said substrate and an exposed outer surface, comprising:
- means for deforming a predetermined area of the exposed outer surface of said layer of wet paint to form a dimple in said layer; and
- means for optically measuring a response of said predetermined area of the exposed outer surface and the time required for said response, the viscosity of the wet paint being a function of said response and said time.

12. An apparatus in accordance with claim 11 wherein said deforming means comprises a gas nozzle, said gas nozzle emitting a brief pulse of compressed gas in order to deform said predetermined area.

13. An apparatus in accordance with claim 11 wherein said optical measuring means further comprises:
- a collimated light source, said light source reflecting a collimated light beam off of said predetermined area;
- means for measuring the intensity of the light reflected off of said predetermined area; and
- means for measuring the time required for the measured reflected light intensity to drop below a threshold level, said threshold level being the level of reflected light intensity from the exposed outer surface after said outer surface initially deforms.

14. An apparatus in accordance with claim 13 wherein said measuring means is a directional spot light meter.

15. An apparatus in accordance with claim 11 wherein said predetermined area is on a painted surface of an automobile.

16. A method of measuring the viscosity of wet paint comprising the steps of:
- providing a substrate having a layer of wet paint thereon, said layer of wet paint having an inner surface adjacent to said substrate and an exposed outer surface;
- reflecting a collimated light beam off of a predetermined area of the exposed surface;
- measuring the intensity of the light reflected off of the predetermined area;
- energizing a jet of compressed gas, said jet emitting a sufficient amount of compressed gas onto the predetermined area to deform the predetermined area of the exposed outer surface;
- determining a threshold level of reflected light intensity from the predetermined area of the exposed outer surface after said outer surface initially deforms;
- measuring a deformation time required for the intensity of the reflected light to drop below the threshold level;
- de-energizing the jet of compressed gas after the reflected light intensity drops below the threshold level;
- measuring a restoration time required for the reflected light intensity to reach the threshold level after the jet of compressed air has been turned off; and
- analyzing the deformation time and the restoration time, thereby determining the viscosity of the layer of paint on the substrate.

17. A method for measuring the viscosity of a layer of wet paint comprising the steps of:
- providing a substrate having a layer of wet paint thereon, said layer of wet paint having an inner surface adjacent to said substrate and an exposed outer surface having an original shape;
- applying a deforming force to a predetermined area of the exposed outer surface of said layer of wet paint to depress said outer surface toward said inner surface to form a dimple in said layer of wet paint and then releasing said deforming force;
- measuring the time required for said outer surface to return to said original shape;
- determining the viscosity of the layer of wet paint based on said time measured.

* * * * *